United States Patent [19]

Ueda et al.

[11] Patent Number: 5,396,889
[45] Date of Patent: Mar. 14, 1995

[54] STEREOTACTIC RADIOSURGERY METHOD AND APPARATUS

[75] Inventors: Hisaki Ueda; Takayuki Nagaoka, both of Kashiwa, Japan

[73] Assignee: Hitachi Medical Corporation, Tokyo, Japan

[21] Appl. No.: 117,324

[22] Filed: Sep. 7, 1993

[30] Foreign Application Priority Data

Sep. 7, 1992 [JP] Japan .................. 4-238661

[51] Int. Cl.$^6$ ............... A61B 6/00; G21K 1/02; G21K 3/00
[52] U.S. Cl. .................. 128/653.1; 378/65; 378/68; 378/147; 378/148; 250/363.1; 250/370.09
[58] Field of Search ............... 128/653.1; 250/363.1, 250/370.07.370.09; 378/65, 147, 148, 68

[56] References Cited

U.S. PATENT DOCUMENTS

| | | | |
|---|---|---|---|
| 4,359,642 | 11/1982 | Heinz et al. | 378/148 |
| 4,489,426 | 12/1984 | Grass et al. | 378/147 |
| 4,998,268 | 3/1991 | Winter | 378/147 |
| 5,019,713 | 5/1991 | Schmidt | 378/65 |
| 5,233,990 | 8/1993 | Barnea | 128/653.1 |

FOREIGN PATENT DOCUMENTS

| | | | |
|---|---|---|---|
| 0060771 | 9/1982 | European Pat. Off. | 128/653.1 |
| 8905171 | 6/1989 | European Pat. Off. | |
| 9202277 | 2/1992 | European Pat. Off. | 128/653.1 |
| 0553766 | 10/1977 | U.S.S.R. | 378/65 |

*Primary Examiner*—Krista M. Pfaffle
*Attorney, Agent, or Firm*—Antonelli, Terry, Stout & Kraus

[57] ABSTRACT

Radiation is generated toward a patient. A radiographic region of the radiation covers a predetermined field-of-view. Both of a stereotactic radiation producing filter and a radiographic radiation producing filter are transported in such a way that the stereotactic radiation producing filter and the radiographic radiation producing filter sequentially intercept the beam axis between the patient and a generation position for the radiation. When the stereotactic radiation producing filter is located on the beam axis, it forms the radiation into radiation required for stereotactic radiosurgery. When the radiographic radiation producing filter is located on the beam axis, it forms the radiation into radiation required for radioscopy. Radiation present within the radiographic region is detected with employment of a radiation detecting unit positioned opposite to the generation position of the radiation with respect to the patient. The radiation is generated when the stereotactic radiation producing filter is located on the beam axis and the radiographic radiation producing filter is located on the beam axis.

14 Claims, 5 Drawing Sheets

STEREOTACTIC RADIOSURGERY METHOD AND APPARATUS

BACKGROUND OF THE INVENTION

The present invention relates to a stereotactic radiosurgery method and a stereotactic radiosurgery apparatus for collectively projecting radiation (containing X-rays and gamma rays etc.) to a lesion of a patient for therapy.

One conventional stereotactic radiosurgery apparatus has been described in WO 89/05171. In this prior art apparatus, the X-ray beams are collimated by the stereotactic collimator mounted on the tip portion of the gantry, the treatment couch is rotated around the vertical axis, whereas the gantry is rotated around the horizontal axis, whereby the X-ray beams are projected to the lesion at various angles within the wide range. As a result, absorbed dose of a normal tissue (namely, no diseased tissue) located around the lesion is considerably lowered, as compared with absorbed dose of this lesion. Since the stereotactic radiosurgery apparatus owns such a feature, if the lesion would be located at the radiation projection position at high precision, effective therapy effects could be achieved. However, if the lesion would be positionally shifted from this radiation projection position, great damage would be given to the normal tissue of the patient. As a consequence, a position of the lesion of a patient must be positionally and continuously coincident with a radiation position at very high precision in the stereotactic radiosurgery method.

The method for positionally making the position of the lesion coincident with the radiation position will now be explained. First, a diagnosing apparatus (CT, MRI, simulator etc.) is employed to relatively calculate the position of the lesion with regard to such a base as a patient fixing member and a mark indicated on a skin of the patient. Subsequently, the patient is transported to a treatment couch, so that a basic point is positionally coincident with a radiation point. Finally, the treatment is moved only by a distance corresponding to a shift between the lesion and the basic point.

Alternatively, a lineacgraphy is employed to determine the radiation position. A "lineacgraphy" implies radioscopy with employment of radiation from a therapy accelerator. At this time, even when a radiographic image is acquired by utilizing such a narrow X-ray beam used in the stereotactic radiosurgery, it cannot be recognized to which portion of the patient, such a narrow X-ray beam is projected. To judge an anatomical position of the lesion, the stereotactic collimator is removed and thereafter a radiographic image thereof must be acquired under a wide radioscopic region.

SUMMARY OF THE INVENTION

In the above-described conventional stereotactic radiosurgery apparatus, even when the lesion could be positionally coincident with the radiation position before stereotactic radiosurgery, there is no way to judge to which portion of the patient, the radiation would be projected during stereotactic radiosurgery. As a result, the lesion is positionally shifted due to movements of the patient such as breath and cardiac beats of the patient under therapy.

An object of the present invention is to provide a stereotactic radiosurgery method and a stereotactic radiosurgery apparatus capable of monitoring movements of a lesion, even while stereotactic radiosurgery is carried out.

To achieve such an object, a stereotactic radiosurgery apparatus according to one aspect of the present invention, comprises:

a radiation generating unit for generating radiation toward a patient, a radioscopic region of said radiation covering a predetermined field-of-view;

a supporting member having a stereotactic radiation producing portion and a radiographic radiation producing portion, said supporting member being movable in such a manner that both of said stereotactic radiation producing portion and said radiographic radiation producing portion sequentially intercept said treatment field between a generation position for said radiation and said patient, said stereotactic radiation producing unit forming said radiation into radiation required for stereotactic radiosurgery when said stereotactic radiation producing portion is located on the beam axis, and said radiographic radiation producing portion forming said radiation into radiation required for radioscopy when said radiographic radiation producing portion is located on the beam axis;

a unit for transporting said supporting member;

a control unit for controlling said radiation generating means in such a manner that said radiation is generated from said radiation generating unit when said stereotactic radiation producing portion is located on the beam axis, and when said radiographic radiation producing portion is positioned on the beam axis; and a radiation detecting unit positioned opposite to said generation position of the radiation with respect to said patient, for detecting radiation within said radioscopic region.

According to this stereotactic radiosurgery apparatus, if the moving speed of the supporting member is increased, a time difference between the projection timing for the stereotactic radiation and the projection timing for the radiographic radiation becomes small. As a consequence, when the moving speed of the supporting member is higher than a preselected speed, this condition is essentially equal to no time difference. Accordingly, it can be achieved that the movements of the patient is monitored based on the detection signal derived from the radiation detecting unit at the same time while the stereotactic radiosurgery is performed.

In accordance with another aspect of the present invention, a stereotactic radiosurgery method comprise the steps of:

generating radiation toward a patient, a radioscopic region of said radiation covering a predetermined field-of-view;

transporting a stereotactic radiation producing portion and a radiographic radiation producing portion in such a manner that both of said stereotactic radiation producing portion and said radiographic radiation producing portion sequentially intercept the beam axis between a generation position for said radiation and said patient, said radiographic radiation producing portion forming said radiation into radiation required for stereotactic radiosurgery when said radiographic radiation producing portion is located on the beam axis, and said radiographic radiation producing portion forming said radiation into radiation required for radioscopy when said radiographic radiation producing portion is located on the beam axis; and detecting radiation present within the radioscopic region by employing radiation detecting means positioned opposite to said generation position of the radiation with respect to said patient, for detecting radiation within said radioscopic region.

The above-described step for generating the radiation includes a step for generating said radiation when said stereotactic radiation producing portion is located on the beam axis, and when said radiographic radiation producing portion is located on the beam axis.

DESCRIPTION OF THE PREFERRED EMBODIMENTS

Figure 1:
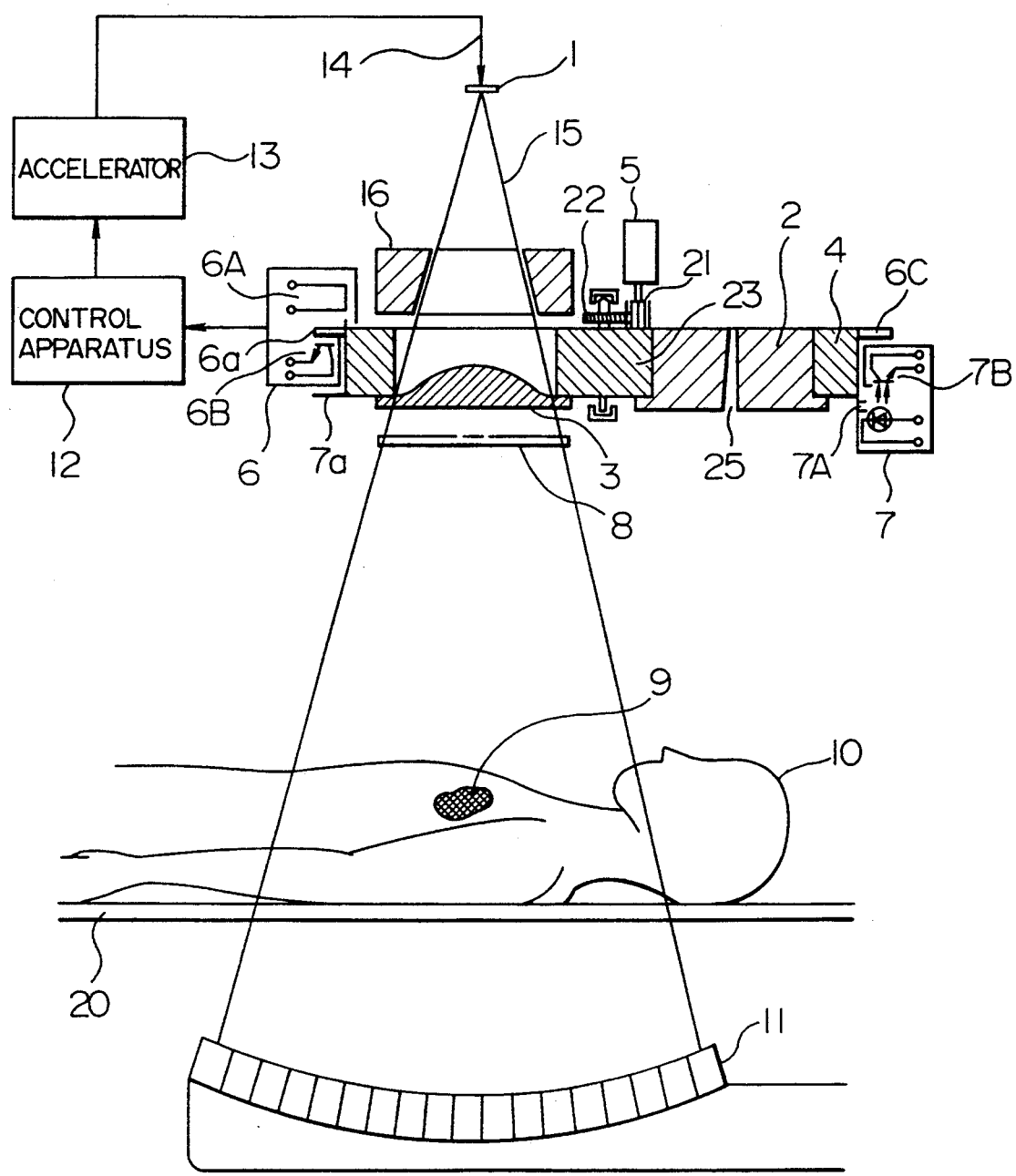
FIG. 1 schematically shows an apparatus for stereotactic radiosurgery according to a preferred embodiment of the present invention.

In FIG. 1, there is shown an apparatus for stereotactic radiosurgery according to one preferred embodiment of the present invention. An electron beam 14 emitted from an accelerator 13 collides with an X-ray target 1 to emit an X-ray 15. A shape of this emitted X-ray 15 is conical. As represented in FIG. 1, this conical shape of the X-ray 15 is collimated into a predetermined shape by way of a primary collimator 16. A field of the X-ray collimated by the primary collimator 16, may cover a preselected radioscopic region. A patient 10 is mounted on a treatment couch 20, to which X-rays (other radiation such as gamma rays are projected in order to perform therapy. A multi-element X-ray detector 11 for detecting X-rays present within the radiation field is provided along the penetration direction of the X-rays. Based upon a detection signal derived from this multi-element X-ray detector 11, a radiographic image (radiogram) of the patient 10 is produced for a monitoring purpose, for example. This X-ray detector 11 is positioned opposite to the position for generating the X-rays.

Figure 2:
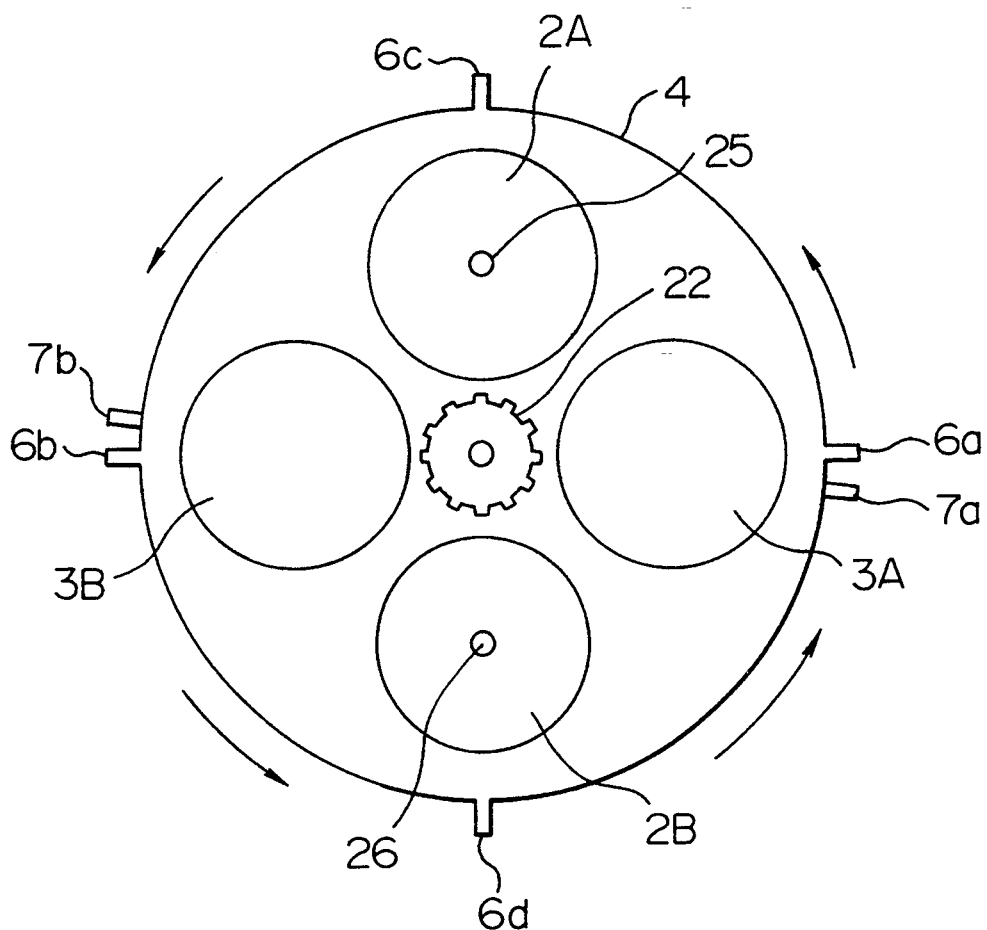
FIG. 2 is an illustration of one example of a collimator holder.

Also, as illustrated in FIG. 1, a collimator or filter holder 4 is provided between the primary collimator 16 and the patient 10. The collimator or filter holder 4 is a circular rotary member rotated by a gear 22 coupled to a drive shaft 21 of a drive apparatus (motor 5). In FIG. 1, there is shown a sectional view of this collimator holder 4, and in FIG. 2, there is represented an upper view of the collimator holder 4. As illustrated in FIG. 2, the collimator holder 4 includes stereotactic collimators or filters 2A and 2B, and flattening filters 3A and 3B, which are alternately arranged along the circular direction at 90° intervals. This collimator holder 4 further includes projection portions for detecting positions 6a, 6b, 6c, 6d, and also identification projection portions 7a, 7b at the outermost portion. These position-detecting projection portions 6a to 6d are formed at an upper end portion of this outermost portion, whereas the identification projection portions 7a and 7b are provided at a lower end portion thereof.

In this preferred embodiment, the stereotactic collimators or filters 2A and 2B constitute stereotactic radiation producing portions, whereas the flattening filters 3A and 3B constitute radioscopic radiation producing portions. In accordance with this preferred embodiment, the respective collimators 2A, 2B, 3A and 3B sequentially intercept or move across the beam axis between the position for generating the X-rays and the patient 10 by rotating the collimator holder 4.

A detector 6 is employed to detect the projection portions 6a to 6d, and is constructed of a light emitting diode 6A and a phototransistor 6B. The detector 6 detects whether or not the projection portions 6a to 6d pass through this detector 6 by checking whether light emitted from the light emitting diode 6A is transmitted or interrupted to the phototransistor 6B. A detector 7 is employed to detect the projection portions 7a and 7b, and is arranged by a light emitting diode 7A and a phototransistor 7B, and also detects whether or not the projection portions 7a and 7b pass through this detector 7.

The stereotactic collimator 2 (2A and 2B) is such a collimator for producing a spot-shaped X-ray used in the stereotactic radiosurgery, and having spot holes 25 and 26 at a center thereof. Since the X-ray passes through these spot holes 25 and 26, the shape of the passed X-ray becomes a spot. It should be noted that a so-called "variable collimator" may be employed as this collimator 2.

The flattening filter 3 (3A, 3B) is employed to flatten X-rays for therapy along a plane in order to wholly attenuate these X-rays and produce radioscopic X-rays. The flattening filter 3 owns a peak type collimating function by which a constant attenuation can be expected even in the edge portions, and also has a large attenuating peak at a central portion. As a result, a flattened X-ray in an overall plane can be obtained by attenuating the X-ray passing through the central portion, namely an X-ray having a uniform dose distribution. In the stereotactic radiosurgery, the X-ray having large dose is used for curing a lesion, and if such a high-dose X-ray would be widely projected to a portion of a patient during the X-ray radioscopy, it could cause a medical risk for the patient. Therefore, the above-described flattening process has been employed by attenuating the X-ray by the flattening filters 3A and 3B to an allowable degree or dose, as well as by making resolution in a plane uniform.

Figure 3:
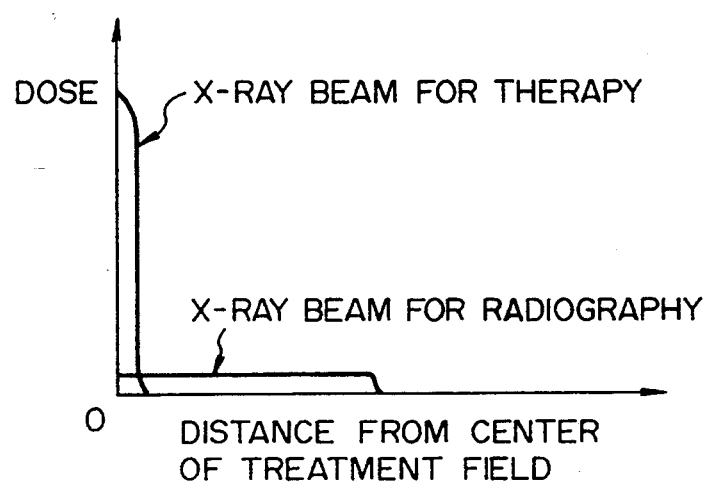
FIG. 3 is a graphic representation for showing characteristics of a stereotactic collimator and a flattening filter, which are mounted on the collimator holder.

In FIG. 3, there is shown output dose of X-rays from the stereotactic collimator and output dose of X-rays from the flattening filter. An abscisa of FIG. 3 denotes a distance (position) from a center of a treatment field. It can be understood from this graphic representation that a spot-shaped X-ray with large dose is obtained by the stereotactic collimator, and also a flattened and attenuated X-ray in a plain field with small dose is obtained by the flattening filter.

A dose monitor 8 is employed for monitoring whether or not dose of X-rays projected to a patient is a proper value.

An accelerator control apparatus 12 controls to generate an electron beam in response to a detection signal indicating whether or not the projection portions pass through the detector 6. That is to say, when a detection signal indicating that the projection portions pass through the detector 6 is inputted into the accelerator control apparatus 12, the electron beam is generated to emit such an X-ray with dose required for stereotactic radiation. In any cases other than the above-explained detection signal, no electron beam is produced so that no X-ray is emitted. As a result, the X-ray is emitted only when the projection portions pass through the detector, so that both of the stereotactic radiosurgery and the radioscopy are carried out. It should also be noted that the accelerator control apparatus 12 may perform not only such a control of generating an X-ray, but also a control for X-ray dose at the same time. In other words, the accelerator control apparatus 12 may control such that dose of X-rays generated when the stereotactic radiation producing portion is located on the beam axis, becomes such a dose required for the stereotactic radio surgery, and also may control such that dose of X-rays generated when the radioscopic radiation producing portion is located on the beam axis, becomes such a dose required for the radioscopy.

As shown in FIG. 2, the reason why the identification projection portions 7a, 7b are provided only with the flattening filters 3A and 3B, and also no identification projection portions are formed on the stereotactic filters 2A and 2B, is to check whether or not the flattening filters 3A and 3B approach, or whether or not the stereotactic collimators 2A and 2B approach. If the detector 6 detects the projections and also the detector 7 detects the projections, the flattening filters 3A and 3B approach to a predetermined position. Although the detector 6 detects the projections, when the detector 7 detects no projection, the stereotactic collimators 2A and 2B approach to a preselected position. When the flattening filters 3A and 3B approach a predetermined position, a value detected by the multi-element detector is utilized by a computer as the radioscopic data. When the stereotactic collimators 2A and 2B approach a preselected position, a value detected from the multi-element detector is utilized by the computer as data used to obtain a shape and a position for an X-ray beam of stereotactic radiation.

Figure 4:
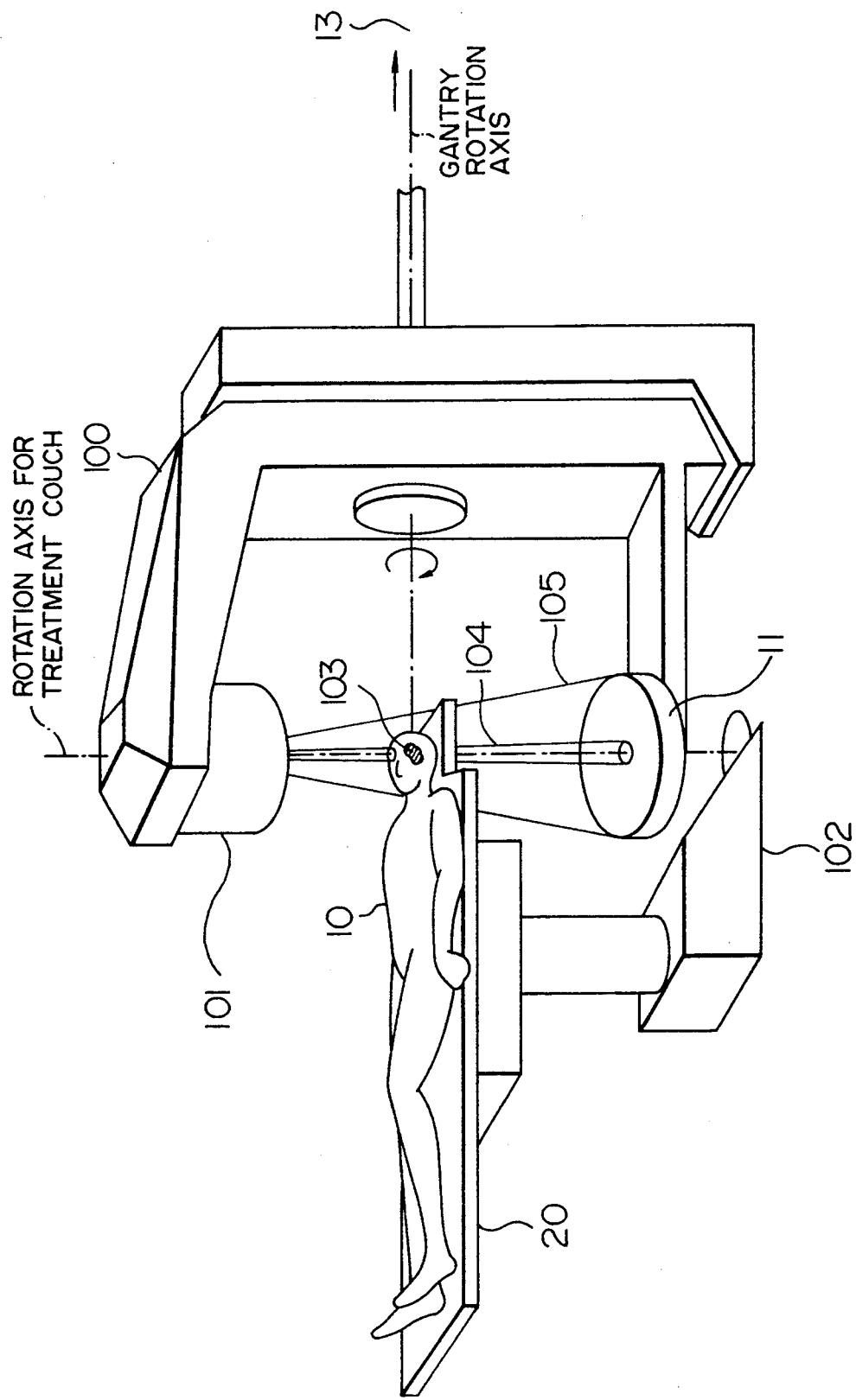
FIG. 4 represents an outer view of the apparatus for stereotactic radiosurgery according to the preferred embodiment of the present invention.

FIG. 4 represents an overall arrangement of the stereotactic radiosurgery apparatus shown in FIG. 1. A gantry 100 receives an electron beam emitted from the accelerator 13 and emits an X-ray through a projection head 101. This gantry 100 is rotated around a rotation axis positioned in parallel to a horizontal axis, and emits the X-ray from the projection head 101, while being rotated. A center of a lesion 103 of a patient 10 laid on the treatment couch 20 is positioned to an isocenter position. Furthermore, a supporting member 102 of the treatment couch 20 is rotated in a unit of a predetermined pitch angle along a vertical axial line, as indicated by an arrow. The supporting member 102 is stopped at each of the pitch angles, during which the gantry 100 is rotated around this lesion 103 to project the spot-shaped X-ray to this lesion 103.

To the projection head 101, as shown in FIG. 1, the X-ray target 1, the primary collimator 16, the collimator holder 4, and the dose monitor 8 are mounted. The collimator holder 4 is being rotated, by which both of the stereotactic collimators 2A, 2B, and the flattening filters 3A, 3B alternately appear on the X-ray projection path at the 90° interval. As a consequence, an alternate selection is made between the stereotactic collimator and the flattening filter in accordance with the rotation speed of the collimator holder 4, so that the stereotactic radiosurgery by the X-ray beam for therapy 104, and the radioscopy by the X-ray beam for radioscopy 105 can be carried out. If the rotation speed of the collimator holder is increased, a time difference between the output of the narrow X-ray used for stereotactic radiosurgery and the output of the wide and flattened X-ray used for radioscopy may be made small. Then, when the rotation speed becomes higher than a predetermined speed, it may be visually recognized as if a radioscopic image can be obtained, while executing stereotactic radiosurgery.

A radioscopic image obtained in this process operation is used to detect positional displacement of the lesion from the isocenter. The radioscopic image is obtained at a high speed, and also a condition of this positional displacement for the lesion with respect to the isocenter is identified from the radioscopic image at a high speed. This positional displacement may be obtained from the detection signal outputted from the detector 11 by performing the well known calculation process. Once such a positional displacement can be determined, the positional control for the gantry 100 and the positional control for the supporting member 102 are automatically executed in order to reduce an amount of this positional displacement to zero. In this case, it should be understood that both of the gantry 100 and the supporting member 102 can be positionally controlled. As a consequence, the positional displacement caused by movements of the lesion and the like can be corrected, while executing the stereotactic radiosurgery.

Furthermore, while displaying a radioscopic image on such a monitor as a CRT (cathode-ray tube), an operator monitors this radioscopic image, whereby he can recognize such a positional displacement of the lesion. As a result, the positional control may be carried out in accordance with the instruction issued by the operator. In this case, no automatic identification and automatic positional control are longer required.

Figure 5:
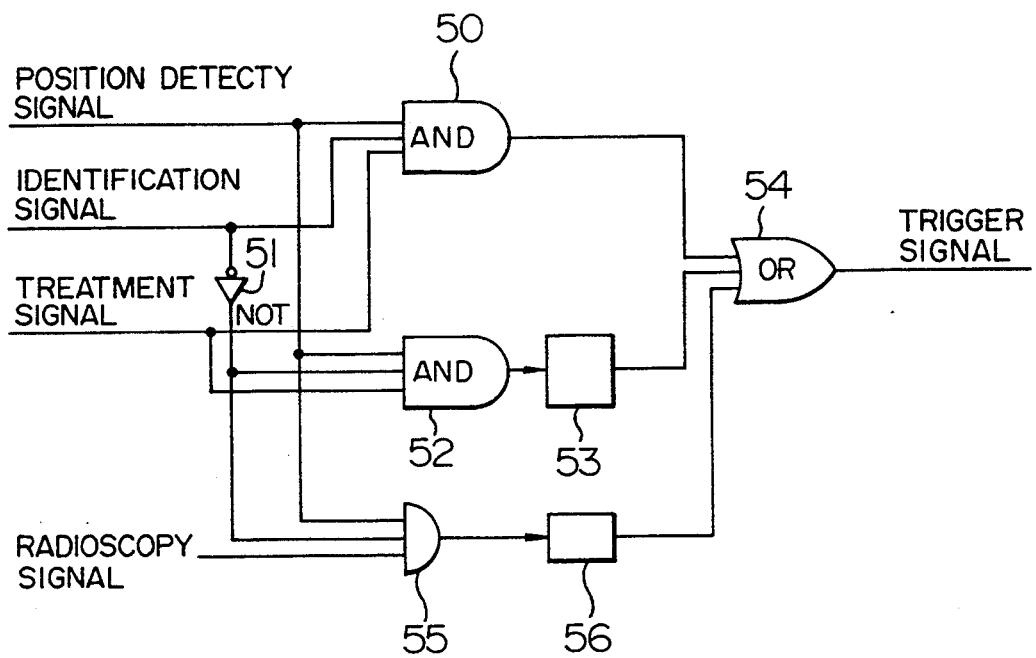
FIG. 5 is a circuit block diagram for showing one example of an electron-beam generation controlling circuit.

Although the stereotactic radiosurgery is performed and the radioscopic image is acquired every 90° in the preferred embodiment shown in FIGS. 1 and 2, there are some possibilities that such a radioscopic image must be frequently acquired, as described in this preferred embodiment. Also, there are some cases that a projection amount of X-rays for radioscopy is essentially reduced by making a long interval to acquire the radioscopic image. In FIG. 5, there is shown an electron-beam generation controlling circuit employed in the accelerator control apparatus 12, by which the intervals capable of acquiring the radioscopic images may be arbitrarily set. This electron-beam generation controlling circuit is arranged by AND gates 50, 52, 55, an inverter 51, interval setting counters 53, 56, and an OR gate 54. It should be noted in FIG. 5 that an externally supplied position detecting signal corresponds to a signal derived from the detector 6 when the projection portions 6a to 6d pass through this detector, whereas an identification signal corresponds to a signal derived from the detector 7 when the projection portions 7a and 7b pass through this detector. Also, a treatment signal corresponds to a signal generated in response to an instruction of the stereotactic radiosurgery. While this treatment signal is generated, the stereotactic radiosurgery is carried out. Further, a radioscopy signal corresponds to such a signal produced in such a case that a radioscopic image is acquired in the stereotactic radiosurgery.

An operation of the electron-beam generation controlling circuit shown in FIG. 5 will now be described.

(1) In case that the treatment signal is produced, the AND gate 50 issues a "1" signal since both of the position detecting signal and the identification signal are produced. This case corresponds to such a case that, as apparent from FIG. 2, the stereotactic collimators 2A and 2B pass through the detector. This "1" output signal from the AND gate 50 passes through the OR gate 54 and then becomes a trigger signal used to produce an electron beam, so that the electron beam is generated. As a consequence, the stereotactic radiosurgery is realized. On the other hand, when the identification signal becomes "0", although the position detecting signal is generated, the AND gate 52 produces a "1" signal. This corresponds to such a case that the flattening filters 3A and 3B pass through the detector. The counter 53 counts the quantity of the "1" output signals issued from the AND gate 52, and a count value for a carry out is settable. If "N" is applied as this settable value to this counter 53, then a carry-out output "1" is produced when the number of the output "1" of the AND gate 52 becomes "N", so that the electron-beam trigger signal is generated through the OR gate 54. In this case, the passing collimator corresponds to the flattening collimator, so that the flattening collimators 3A and 3B successively pass through the detector, and the radioscopic X-rays are emitted every time "N" pieces of flattening collimators pass through the detector. It should be noted that this number "N" may be arbitrarily selected, and therefore the interval for stereotactic radiosurgery may be adjusted by this number "N".

(2) When only the radioscopy signal is issued, an arbitrary interval is set via a counter 56 to an output signal from the AND gate 55. A set value for this counter 56 is settable similar to the above-explained counter 53.

Figure 6:
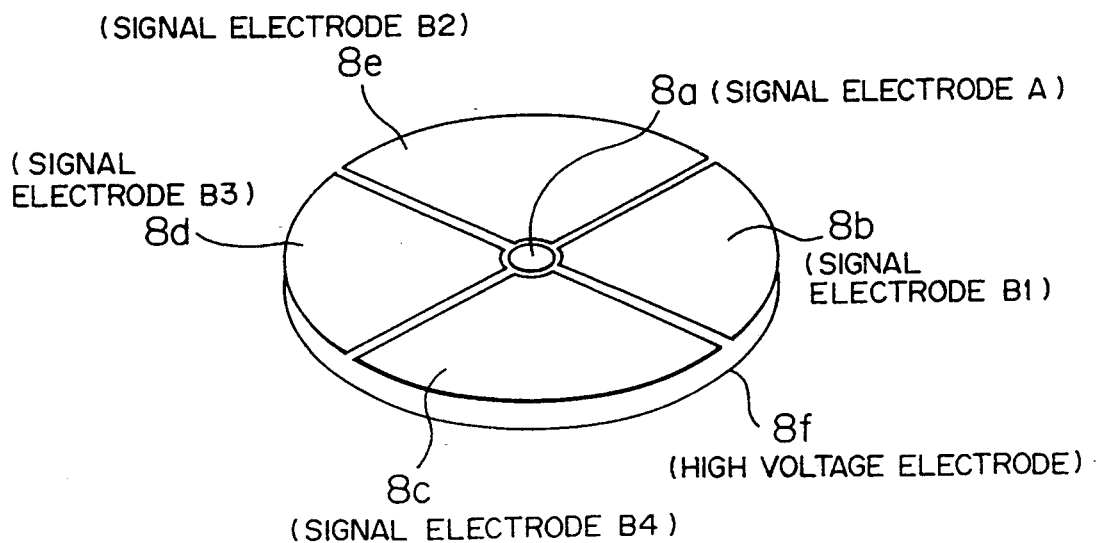
FIG. 6 schematically shows a dose monitor used in the collimator holder.

FIG. 6 represents one example of a dose monitor 8 utilized in the present invention. This dose monitor 8 corresponds to a transmission parallel plate type ionization chamber. A high voltage is being applied to a high voltage electrode. A signal electrode "A" is employed to monitor the dose of a stereotactic radiosurgery X-ray, whereas signal electrodes B1, B2, B3 and B4 are employed to monitor the dose of a radioscopy X-ray, and furthermore to monitor a dose distribution.

It should be understood that an electron accelerator such as lineac and microtron normally produces such an electron beam having a pulse width of approximately 5 microseconds at an interval of about 5 milliseconds. In case that the collimator holder as illustrated in FIG. 2 is used, a rotation period of this collimator holder becomes approximately 20 milliseconds (5 ms×4) in accordance with the operation period of the accelerator. On the other hand, a pulse width of this electron beam is selected to be about 5 microseconds, and corresponds to 1/4000 of the rotation period of the collimator holder. Accordingly, it can be regarded that the collimator holder is stopped while the electron beam is outputted or emitted.

Figure 7:
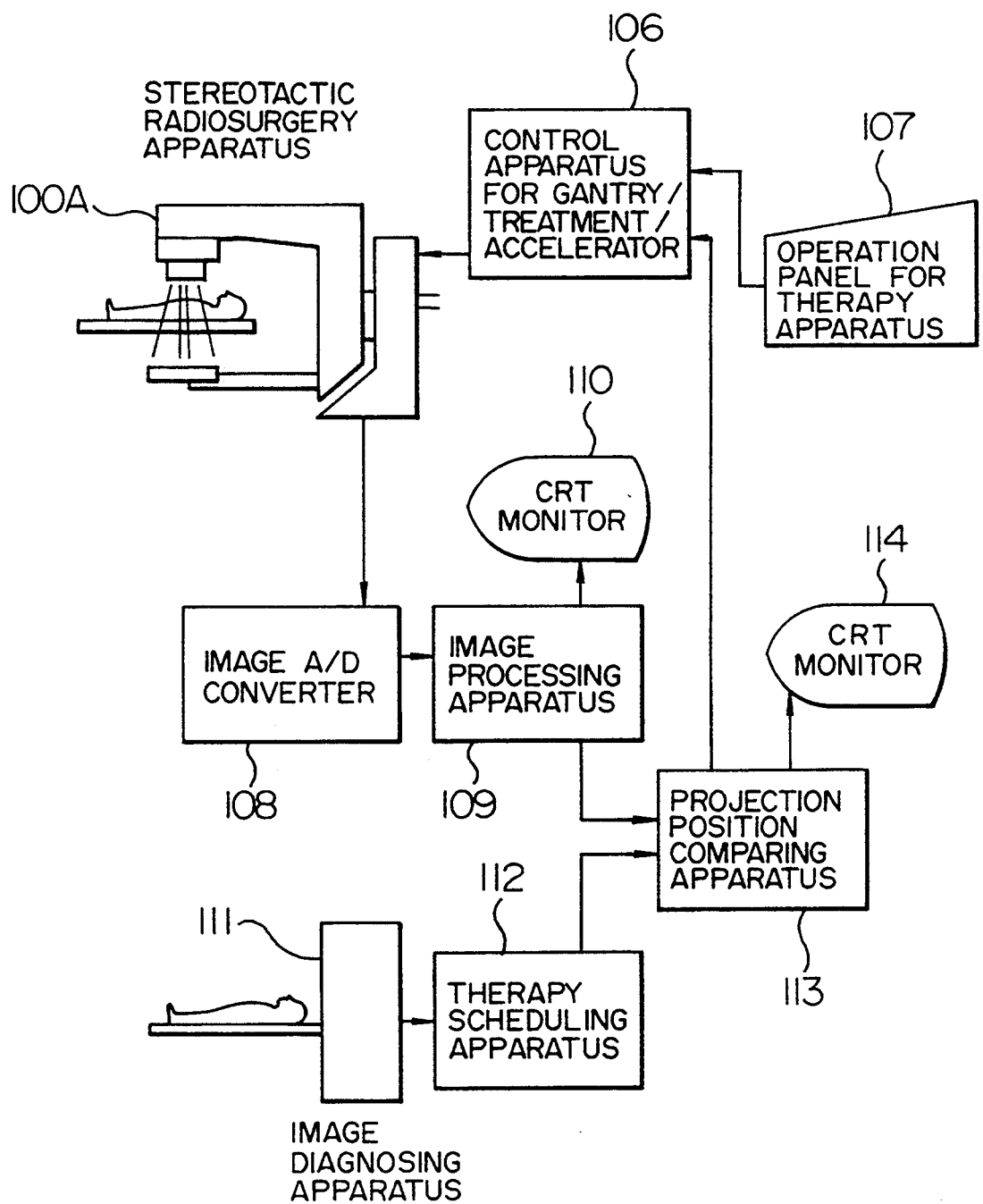
FIG. 7 is a schematic diagram for indicating an example of a stereotactic therapy system including the stereotactic radiosurgery apparatus according to the preferred embodiment of the present invention.

FIG. 7 represents one example of a stereotactic radiosurgery system. This stereotactic radiosurgery system is arranged by, as shown in FIGS. 1 and 4, a stereotactic radiosurgery apparatus 100A, a control apparatus 106 for gantry/treatment couch/accelerator, an A/D converter 108, an operation panel 107 for therapy apparatus, and an image processing apparatus 109. Furthermore, this radiosurgery system further includes CRT monitors 110, 114, a projection position comparing apparatus 113, a therapy scheduling apparatus 112, and an image diagnosing apparatus 111. First, a position and a condition of a lesion are considered by the image diagnosing apparatus 111, and the resultant therapy schedule is formed in the therapy scheduling apparatus 112. In accordance with this therapy schedule, the therapy apparatus 100A performs the stereotactic radiosurgery by the control apparatus 106 in response to an instruction issued from the operation panel 107. On the other hand, a detection signal derived from the multi-element X-ray detector is acquired via the A/D converter 108 into the image processing apparatus 109, so that the positions of the radioscopic image and the therapy X-ray beam are displayed on the CRT monitor 110. This image is also sent to the comparing apparatus 113 by which this image is compared with an image predicted during the therapy scheduling operation, and then such a calculation is carried out for checking where/how much a patient has been shifted along a predetermined direction. The resultant compared image is displayed on the CRT monitor 114, so that an operator can confirm such a positional displacement. The data about the shift direction and the distance are transferred to the control apparatus 106 in order to correct the positional shift by moving the treatment couch.

While the present invention has been described with reference to the preferred embodiments, the present invention is not limited only to these preferred embodiments. For instance, the above-explained preferred embodiment may be modified as follows.

(1) In FIG. 2, a single projection portion having a different width from that of the projection portion may be employed, instead of the projection portions 6a and 7a of the flattening collimator 3A, and similarly, a single projection portion having a different width from that of the projection portions 6c and 6d may be utilized, instead of the projection portions 6b and 7b of the collimator 3B. Also, a slit and the like may be employed, instead of the projection portion.

(2) Although 4 collimators for stereotactic and flattening purposes have been alternately provided on the collimator holder 4 at 90° interval, there is no limitation in this interval and quantity.

(3) The collimator holder 4 is of the rotary type collimator holder in the above-described preferred embodiment. Alternatively, a single stereotactic collimator and a single flattening filter are positioned in a straight line or an arc shape on a collimator holder. This collimator holder may be moved in either a linear fashion, or an arc fashion so as to select one of these stereotactic collimator and flattening filter.

(4) Instead of the multi-element detector, a fluorescent plate for X-ray/fluorescent ray conversion is provided, and a fluorescent ray may be imaged by a TV camera. In this case, a radioscopic image may be directly obtained.

We claim:

1. A stereotactic radiosurgery apparatus comprising:
   a radiation source for generating a radiation beam toward a patient;
   a first filter for filtering said radiation beam into stereotactic radiation;
   a second filter for filtering said radiation beam into radiographic radiation;
   means for positioning one of said first and second filters in a predetermined sequence on a path of the radiation beam between said radiation source and the patient; and
   a detector for detecting said radiation beam which passed through said second filter and the patient.

2. A stereotactic radiosurgery apparatus as claimed in claim 1, further comprising means for forming an image based upon an output signal from said detector.

3. A stereotactic radiosurgery apparatus as claimed in claim 1, further comprising:
   means for generating a first signal indicative of a shift between a first position of a lesion in the patient and a second position of the lesion in the patient based on an output signal from said detector; and
   means for relatively moving said patient with respect to said radiation beam so that said first position is positionally coincident with said second position based on said first signal.

4. A stereotactic radiosurgery apparatus as claimed in claim 1, further comprising:
   means for controlling an intensity of said radiation beam so that when said first filter is positioned in the radiation beam path, said radiation beam provides a first dose appropriate for the stereotactic radiation, and when said second filter is positioned in the radiation beam path, said radiation beam provides a second dose appropriate for the radiographic radiation.

5. A stereotactic radiosurgery apparatus as claimed in claim 1, wherein said positioning means alternately positions said first and second filters in the radiation beam path.

6. A stereotactic radiosurgery apparatus as claimed in claim 1, wherein said positioning means comprises a holder on which said first and second filters are mounted, and a rotator for rotating said holder, respective centers of said first and second filters being substantially positioned on an imaginary circle concentric with a rotational center of said holder, said imaginary circle intersecting the radiation beam path.

7. A stereotactic radiosurgery apparatus as claimed in claim 6, wherein said first and second filters are positioned on said imaginary circle alternately.

8. A stereotactic radiosurgery apparatus comprising:
   means for generating a radiation beam toward a patient;
   first filter means for forming said radiation beam into a first beam of stereotactic radiation;
   second filter means for forming said radiation beam into a second beam of radiographic radiation;
   means for positioning one of said first and second filter means in a predetermined sequence in a path of said radiation beam between said generating means and the patient; and
   means for detecting said second beam which passed through said second filter means and the patient.

9. A stereotactic radiosurgery method comprising the steps of:
   generating a radiation beam toward a patient;
   positioning one of a first filter for stereotactic radiation and a second filter for radiographic radiation in a predetermined sequence in a path of the radiation beam directed toward the patient; and
   detecting the radiation beam which passed through the second filter and the patient.

10. A stereotactic radiosurgery method as claimed in claim 9, further comprising the steps of:
    determining which one of the first and second filters is positioned in the radiation beam path;
    changing a dose of the radiation beam based on a result of the determining step so that when said first filter is positioned in the radiation beam path, the radiation beam provides a first dose appropriate for the stereotactic radiation, and when said second filter is positioned in the radiation beam path, the radiation beam provides a second dose appropriate for the radiographic radiation.

11. A radiation beam controlling apparatus comprising:
    a holder on which a first filter for stereotactic radiation and a second filter for radiographic radiation are mounted; and
    a rotator for rotating said holder;
    wherein respective centers of said first and second filters are substantially positioned on an imaginary circle concentric with a rotational center of said holder, said imaginary circle intersecting a path of a primary radiation beam from a radiation source.

12. A radiation beam apparatus as claimed in claim 11, wherein said first and second filters are positioned on said imaginary circle alternately.

13. A radiation beam controlling device comprising:
    a first filter for stereotactic radiation;
    a second filter for radiographic radiation; and
    means for holding said first filter and said second filter so that respective centers of said first and second filters are substantially positioned on an imaginary circle concentric with a rotational center of said holder, said imaginary circle intersecting a path of a primary radiation beam from a radiation source.

14. A device as claimed in claim 13, wherein said first and second filters are positioned on said imaginary circle alternately.

* * * * *